(12) United States Patent
Feldman

(10) Patent No.: US 7,121,982 B2
(45) Date of Patent: Oct. 17, 2006

(54) COMPUTER INTERACTIVE ISOMETRIC EXERCISE SYSTEM AND METHOD FOR OPERATIVELY INTERCONNECTING THE EXERCISE SYSTEM TO A COMPUTER SYSTEM FOR USE AS A PERIPHERAL

(75) Inventor: Philip Feldman, Catonsville, MD (US)

(73) Assignee: PowerGrid Fitness, Inc., Bethesda, MD (US)

( * ) Notice: Subject to any disclaimer, the term of this patent is extended or adjusted under 35 U.S.C. 154(b) by 173 days.

(21) Appl. No.: 10/309,565

(22) Filed: Dec. 4, 2002

(65) Prior Publication Data

US 2004/0110602 A1   Jun. 10, 2004

(51) Int. Cl.
*A63B 21/00* (2006.01)

(52) U.S. Cl. .................... 482/8; 482/1; 482/9; 482/900

(58) Field of Classification Search ............... 482/1–9, 482/57, 91, 900–902; 601/23, 33, 34
See application file for complete search history.

(56) References Cited

U.S. PATENT DOCUMENTS

| | | | |
|---|---|---|---|
| D188,376 S | 7/1960 | Hotkins et al. | |
| 3,428,312 A | 2/1969 | Machen | |
| 4,296,931 A | 10/1981 | Yokoi | |
| 4,337,050 A | 6/1982 | Engalitcheff, Jr. | |
| 4,494,754 A | 1/1985 | Wagner, Jr. | |
| 4,630,817 A | 12/1986 | Buckley | |
| 4,680,577 A | 7/1987 | Straayer et al. | |
| 4,691,694 A * | 9/1987 | Boyd et al. ................ | 601/34 |
| 4,711,447 A | 12/1987 | Mansfield | |
| 4,742,832 A | 5/1988 | Kauffmann et al. | |
| D318,073 S | 7/1991 | Jang | |
| 5,054,771 A | 10/1991 | Mansfield | |
| 5,089,960 A | 2/1992 | Sweeney, Jr. | |
| 5,104,119 A | 4/1992 | Lynch | |
| 5,116,296 A * | 5/1992 | Watkins et al. .............. | 482/91 |
| 5,199,875 A | 4/1993 | Trumbull | |
| 5,299,810 A | 4/1994 | Pierce et al. | |
| 5,360,383 A * | 11/1994 | Boren ........................ | 482/10 |

(Continued)

FOREIGN PATENT DOCUMENTS

WO   WO 91/11221   8/1991
WO   WO 00/57387 A1   9/2000

OTHER PUBLICATIONS

Glas, V; "Chair Puts Player on the Joystick"; Machine Design; Penton, Inc., vol. 63, No. 21, Oct. 24, 1991; p. 73.

(Continued)

*Primary Examiner*—Glenn E. Richman
(74) *Attorney, Agent, or Firm*—Edell, Shapiro & Finnan, LLC

(57) ABSTRACT

A computer interactive isometric exercise system includes an effector, a sensor coupled at a selected location on the effector to measure a force applied by a user to the effector, where the applied force effects a strain on the effector, and control circuitry. The control circuitry includes a processor that receives and processes data corresponding to applied force information measured by the sensor for transference to a host computer. The processed data is transferred in a format compatible with the host computer and facilitates user interaction with the host computer in response to effector manipulation by the user. A plurality of effectors may further be combined together to form a system frame that provides a variety of isometric exercises for the user in combination with user interaction with the host computer.

28 Claims, 2 Drawing Sheets

U.S. PATENT DOCUMENTS

| | | | |
|---|---|---|---|
| 5,362,298 | A | 11/1994 | Brown et al. |
| 5,368,546 | A * | 11/1994 | Stark et al. .................... 601/34 |
| 5,431,569 | A | 7/1995 | Simpkins et al. |
| 5,462,503 | A | 10/1995 | Benjamin et al. |
| 5,466,200 | A | 11/1995 | Ulrich et al. |
| 5,547,439 | A | 8/1996 | Rawls et al. |
| 5,551,693 | A | 9/1996 | Goto et al. |
| D376,826 | S | 12/1996 | Ashida |
| 5,584,700 | A | 12/1996 | Feldman et al. |
| 5,591,104 | A | 1/1997 | Andrus et al. |
| D384,115 | S | 9/1997 | Wilkinson et al. |
| 5,669,773 | A | 9/1997 | Gluck |
| 5,689,285 | A | 11/1997 | Asher |
| 5,690,582 | A | 11/1997 | Ulrich et al. |
| 5,713,794 | A | 2/1998 | Shimojima et al. |
| 5,716,274 | A | 2/1998 | Goto et al. |
| 5,785,630 | A | 7/1998 | Bobick et al. |
| D397,164 | S | 8/1998 | Goto |
| 5,792,031 | A | 8/1998 | Alton |
| D402,317 | S | 12/1998 | Goto |
| 5,853,326 | A | 12/1998 | Goto et al. |
| 5,889,507 | A | 3/1999 | Engle et al. |
| D407,758 | S | 4/1999 | Isetani et al. |
| 5,890,995 | A | 4/1999 | Bobick et al. |
| 5,901,612 | A | 5/1999 | Letovsky |
| 5,904,639 | A | 5/1999 | Smyser et al. |
| D411,258 | S | 6/1999 | Isetani et al. |
| 5,921,899 | A | 7/1999 | Rose |
| 5,929,782 | A | 7/1999 | Stark et al. |
| 5,947,824 | A | 9/1999 | Minami et al. |
| 5,980,256 | A | 11/1999 | Carmein |
| 5,989,157 | A * | 11/1999 | Walton ........................... 482/4 |
| D421,070 | S | 2/2000 | Jang et al. |
| 6,044,772 | A | 4/2000 | Gaudette et al. |
| 6,086,518 | A | 7/2000 | MacCready, Jr. |
| 6,102,832 | A | 8/2000 | Tani |
| D431,051 | S | 9/2000 | Goto |
| D434,769 | S | 12/2000 | Goto |
| D434,770 | S | 12/2000 | Goto |
| 6,203,432 | B1 | 3/2001 | Roberts et al. |
| 6,216,547 | B1 | 4/2001 | Lehtovaara |
| D441,369 | S | 5/2001 | Goto |
| 6,228,000 | B1 | 5/2001 | Jones |
| 6,231,444 | B1 | 5/2001 | Goto et al. |
| D444,469 | S | 7/2001 | Goto |
| 6,296,595 | B1 | 10/2001 | Stark et al. |
| 6,325,767 | B1 | 12/2001 | Wolff et al. |
| 6,359,613 | B1 | 3/2002 | Poole |
| D456,410 | S | 4/2002 | Ashida |
| D456,854 | S | 5/2002 | Ashida |
| D457,570 | S | 5/2002 | Brinson |
| 6,388,655 | B1 | 5/2002 | Leung |
| 6,394,905 | B1 | 5/2002 | Takeda et al. |
| D459,727 | S | 7/2002 | Ashida |
| D460,506 | S | 7/2002 | Tamminga et al. |
| D462,683 | S | 9/2002 | Ashida |
| D471,594 | S | 3/2003 | Nojo |
| 6,568,334 | B1 | 5/2003 | Gaudette et al. |
| 6,616,579 | B1 | 9/2003 | Reinbold et al. |
| 6,636,161 | B1 | 10/2003 | Rosenberg |
| 6,663,058 | B1 | 12/2003 | Peterson et al. |
| 6,726,566 | B1 | 4/2004 | Komata |
| D500,100 | S | 12/2004 | van der Meer |
| D510,391 | S | 10/2005 | Merril et al. |
| D514,627 | S | 2/2006 | Merril et al. |
| D517,124 | S | 3/2006 | Merril et al. |
| 2001/0018363 | A1 | 8/2001 | Goto et al. |
| 2002/0185041 | A1 | 12/2002 | Herbst |
| 2003/0069108 | A1 | 4/2003 | Kaiserman et al. |
| 2003/0193416 | A1 | 10/2003 | Ogata et al. |
| 2004/0038786 | A1 | 2/2004 | Kuo et al. |
| 2004/0041787 | A1 | 3/2004 | Graves |
| 2004/0077464 | A1 | 4/2004 | Feldman et al. |
| 2004/0110602 | A1 | 6/2004 | Feldman |
| 2004/0180719 | A1 | 9/2004 | Feldman et al. |
| 2005/0130742 | A1 | 6/2005 | Feldman et al. |

OTHER PUBLICATIONS

"AGH's Atari Project Puffer Page"; http://www.atarihq.com/othersec/puffer/index.html; retrieved from the Internet on Sep. 19, 2002; 4 pages.

"The Legible City"; www.jeffrey-shaw.net; retrieved from the Internet on Sep. 19, 2002; 3 pages.

Antonoff, M.; "Living in a Virtual World"; Popular Science, Jun. 1993; 2 pages.

Antonoff, M.; "Virtual Violence: Boxing without Bruises"; Popular Science, Apr. 1993; 1 page.

Brown, S.; "Video Cycle Race"; Popular Science, May 1989; 1 page.

"Military: Arcade Aces"; Popular Mechanics, Mar. 1982; 1 page.

"Suncom Aerobics Joystick"; www.atarihq.com; retrieved from Internet Sep. 19, 2002; 1 page.

Aukstakalnis, et al.; "The Art and Science of Virtual Reality: Silicon Mirage"; pp. 197-205.

Hamit, F.; "Virtual Reality and the Exploration of Cyberspace"; Jun. 1, 1993, 4 pages.

"The Race Begins with $85"; Randal Sports; 1990; 1 page.

"The New Exertainment System"; Life Fitness; 1995; 1 page.

"The History of Nintendo (1889-1997)"; Retrieved from Internet Aug. 9, 1998; pp. 1 and 9-10.

Skorupa, J.; "Virtual Fitness"; Sports Science, Popular Mechanics; Oct. 1994; 3 pages.

Manning, R.; "Videogame Players Get a Workout with the Exertainment"; The Courier-Journal Sep. 25, 1994; 1 page.

Shah, "Mad Catz Universal MC2 Racing Wheel", Feb. 18, 2005.

"Universal S-Video/Audio Cable", retrieved from the Internet, www.madcatz.com.

* cited by examiner

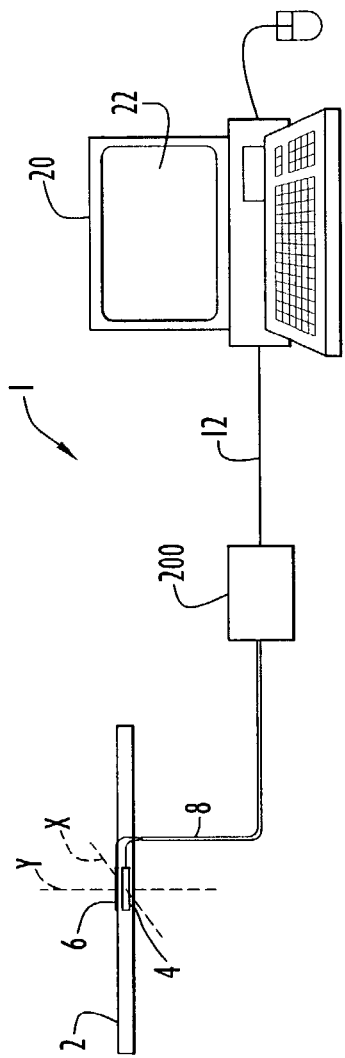
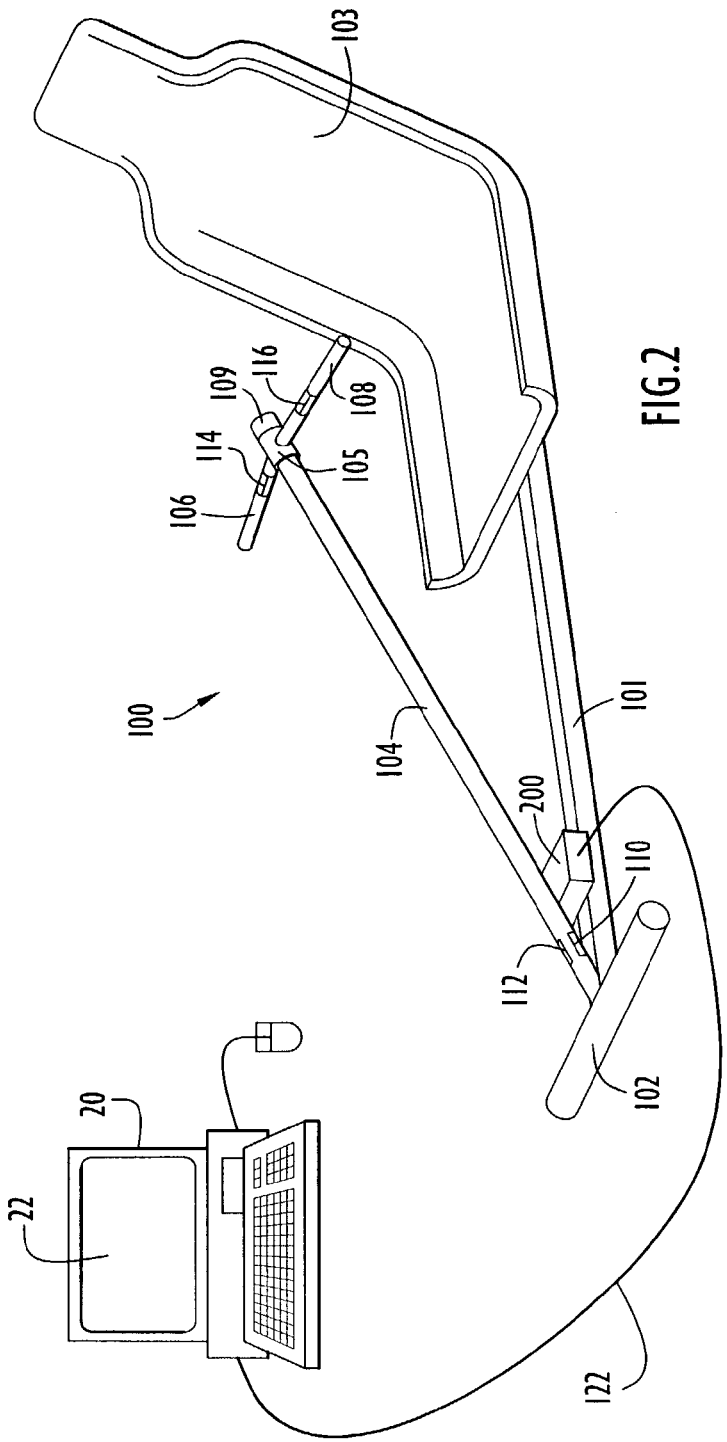
FIG.1
FIG.2

COMPUTER INTERACTIVE ISOMETRIC EXERCISE SYSTEM AND METHOD FOR OPERATIVELY INTERCONNECTING THE EXERCISE SYSTEM TO A COMPUTER SYSTEM FOR USE AS A PERIPHERAL

BACKGROUND OF THE INVENTION

1. Technical Field

The present invention pertains to isometric exercise devices. In particular, the present invention pertains to an isometric exercise system that serves as a computer system peripheral and facilitates user interaction with a host computer system while the user performs isometric exercises.

2. Discussion of the Related Art

Currently, a wide variety of different types of exercise devices are commonly utilized to promote health and fitness, particularly for people having sedimentary lifestyles and/or work environments, and to provide rehabilitation for particular types of injuries. The vast majority of these exercise devices utilize isokinetic and/or isotonic forms of exercise during operation, where a user's muscles are moved under resistance through a selected range of motion.

Isometric exercise is another effective form of muscular exercise that is very useful for rehabilitation, fitness and/or training. For example, isometric training is useful for fighter jet pilots who perform isometric muscular contractions of the lower limbs and body core during flights to prevent blackouts when subjected to high gravitational forces. Isometric exercise involves the exertion of force by a user against an object that significantly resists movement as a result of the exerted force such that there is substantially minimal or no movement of the user's muscles during the force exertion. Examples of simple forms of isometric exercise include pushing against a stationary surface (e.g., a doorframe or a wall), attempting to pull apart tightly gripped hands or to bend or flex a sufficiently rigid steel bar, etc. Due to their inherently tedious nature, isometric exercise devices are less popular and, accordingly, are limited in type and availability, in comparison to more conventional forms of isotonic and isokinetic exercise devices.

A particularly important feature in many isometric exercise devices is the ability to measure forces applied to a resistive object by one or more muscle groups. This is a basic component of biometrics. For example, U.S. Pat. No. 5,904,639 (Smyser et al.) discloses a device including a hand grip recording dynamometer with a load cell mounted therein. The load cell is coupled to a circuit board that is compressively squeezed during an exercise regimen. The device further includes a display to provide visual cues to a user prompting the user as to which hand to use and the amount of compressive squeezing force to be applied. U.S. Pat. No. 6,086,518 (MacCready, Jr.) discloses a similar type of device employing a squeezable exerciser having a body structure with squeezable surfaces and means associated with the body structure to produce reference signals as the level of force application reaches preset limits.

U.S. Pat. No. 4,742,832 (Kauffmann et al.) discloses an apparatus and method for measuring the strength of selected muscles of the human anatomy. The apparatus comprises an upright support frame with a force sensor and measuring device stationarily positioned on the frame. A first force transmitting member carries a patient engageable apparatus to transmit forces along a horizontal axis to actuate the sensor and measuring device. A second force transmitting member carries an additional patient engageable apparatus to transmit forces along a vertical axis, while a force transfer mechanism converts forces transmitted along the vertical axis into horizontal forces transmitted by the first transmitting member. The apparatus further comprises an apparatus for locating the patient in the same position during successive measuring sessions.

U.S. Pat. No. 6,296,595 (Stark et al.) describes an orthopedic restraining device including a housing with first and second distal end portions and restraining means for restraining movement of the first and second distal end portions with respect to each other. The restraining device further includes an elongated straining bar having a stress sensing mechanism for sensing stress on the restraining bar. A control unit, including a microprocessor and a recording mechanism, is provided for indicating sensed stress based upon outputs of the stress sensing mechanism. The elongated straining bar may include an adjustable hinge that is capable of adjusting the angle between the distal end portions.

U.S. Pat. No. 6,228,000 (Jones) discloses a machine for testing the muscle strength of a subject, wherein both static and dynamic strength tests are conducted on the subject. During the tests, forces exerted by the muscles are measured by devices that are connected to a computer and a display screen for displaying the strength of the muscles at different positions of a subject's body part. In the dynamic strength test, the subject moves a movement arm by exerting the muscles to be tested. The movement arm is connected to a resistance weight to oppose movement by the subject. In the static strength test, the movement arm is fixed in position and the subject exerts a body part against the movement arm upon exertion of the muscles to be tested. Force and angle measuring devices are connected to the movement arm and the computer for enabling the muscle strength to be displayed in terms of torque at various angular positions of the body part.

U.S. Pat. No. 6,325,767 (Wolff et al.) describes a strength measuring device for measuring the force-exerting ability of human muscle groups, where the device includes at least one vertically adjustable pressing element that works with a force-measuring unit which can measure the force exerted on the pressing element. The device further includes at least one additional pressing element that is also vertically adjustable and serves to hold certain parts of the test person's body in place.

The previously described exercising devices are limited in that they are tedious and provide limited feedback, generally relating to the amount of force being applied by the user operating the device. An isometric device that provides more enhanced feedback and is entertaining to the user is desirable to increase user interest in the particular isometric exercise so as to ensure continuous and sustained use of the device.

Accordingly, International Publication No. WO 91/11221 (Bond et al.) describes a computer controlled exercise system that sequentially and automatically implements isokinetic, isotonic and isometric exercises to permit a physical therapist to attend to other patients while the computer interacts with the patient to effect a desired therapy. In one embodiment, the motion of a patient's body, such as lifting or twisting the patient's limb, is converted into a runner on a display that competes against another runner. If the patient meets or exceeds the exercise goals, such as a number of repetitions or torque applied to the exercise unit, then the runner representing the patient will match or beat the other runner representing the goal.

Interaction between the exercise system and a computer in the previously described International Publication is limited to simple representations on a display that are based upon achieving set goals and do not provide an indication of the precise amount or degree of force being applied by the user to the exercise device at any given time. Further, this exercise system does not provide a virtual reality interactive environment, where the user is capable of interacting with a computer generated virtual reality scenario to control a variety of movements of a character or an object in the scenario as well as other features relating to the scenario. Those types of scenarios typically utilize a computer interface device to facilitate user interaction with the scenario. A majority of these devices employ strain-based measurement of force. For example, the pointing "nipple" employed in laptop computer system keyboards and the "Force-stick" utilized by high performance aircraft, such as fighter jets, employ strain-based technology. Further, this technology may be employed in various applications ranging from automotive to robotic interfaces. For examples of these applications, reference is made to U.S. Pat. No. 6,216,547 (Lehtovaara) and U.S. Pat. No. 6,388,655 (Leung).

In an attempt to combine virtual reality with an isometric exercise device, an Interactive Video Exercise System (IVES) is disclosed in Dang et al. "Interactive Video Exercise System for Pediatric Brain Injury Rehabilitation", Proceedings of the RESNA 20$^{th}$ Annual Conference, June 1998. This system provides an instrumented video-game-enhanced exercise program for pediatric brain injury patients, where the system includes an isometric test apparatus, a data processing circuit box, and a Super NES™ system with an adapted game controller. The isometric test apparatus includes a first load cell rigidly mounted onto a metal cross-bar that clamps to two rear legs of a chair. A high tensile cable and an ankle band couple the shank of a subject sitting in the chair to the first load cell. A second load cell is mounted between two aluminum plates which rest on the floor. The subject's foot rests on the top plate against a heel stop and is secured with two straps. Isometric extensions of the subject's knee is measured by the first load cell, and isometric ankle dorsiflexion of the subject is measured by the second load cell. The signal from either load cell is transmitted to the data processing box, where it is processed and compared with a variable threshold value set by a potentiometer. When the transducer's signal exceeds the threshold value, voltage is passed to the adapted game controller whereby the selected operation is executed in a game (e.g., move right, move left, move up, move down, etc.). As a result, the subject can only play the game by performing certain isometric exercises.

The previously described IVES system is limited in that a game controller for a Super NES™ system must be adapted to render the system operable. In other words, the IVES system does not have flexibility for use with computer games associated with other computer systems that are incompatible with a Super NES™ system. In addition, the IVES system is limited to isometric knee and ankle exercises and, thus, is incapable of being utilized in a variety of different contexts where it is desirable to exercise upper body parts alone or in combination with lower body parts of a user.

OBJECTS AND SUMMARY OF THE INVENTION

Accordingly, it is an object of the present invention to provide an isometric exercise system that is interactive with a host computer system during user operation so as to enhance the level of interest and enjoyment associated with performing isometric exercises.

It is another object of the present invention to configure the isometric exercise system to determine a type and an amount or degree of force applied by a user to the exercise system.

Yet another object of the present invention is to configure the isometric exercise system to communicate with a host computer system in a recognizable manner so as to facilitate user participation in virtual reality simulation scenarios generated by the host computer system based on performance of isometric exercises on the exercise system.

Still another object of the present invention is to configure the isometric exercise system to be adaptable for use with a wide variety of computer systems capable of running "off-the-shelf" games or other software programs.

A further object of the present invention is to configure the isometric exercise system to be modular in design so as to permit a user to custom design the system for a desired purpose or a particular application.

The aforesaid objects are achieved individually and/or in combination, and it is not intended that the present invention be construed as requiring two or more of the objects to be combined unless expressly required by the claims attached hereto.

According to the present invention, an isometric exercise system serving as a peripheral to facilitate user interaction with a host computer system includes at least one effector, at least one sensor coupled at a selected location on the effector and control circuitry including a processor. The sensor measures at least one force applied by a user to the effector, where the applied force effects a strain on or deflects the effector. The effector may be in the form of a metal rod, where the user applies force (e.g., bending, twisting, tension, compressive forces, etc.) that slightly and measurably deforms the effector within its elastic limit. The processor includes a data processing module to receive and process data corresponding to applied force information measured by the sensor for transference to the host computer system, where the processed data is transferred in a format compatible with the host computer system and facilitates user interaction with the host computer system via effector manipulation by the user. In other words, the processor provides the information to the host computer system in a format similar to that supplied by a conventional computer peripheral or input device. The host computer system processes the information to update or respond to events within an executing software application (e.g., a game). A plurality of effectors may be connected in any suitable manner to each other via one or more suitable connectors to form a frame that can be customized based upon user preference and/or a particular application.

The present invention provides several advantages. One advantage is the ability of the system to be utilized with a number of different types of computer systems in the manner of conventional peripheral devices (e.g., a joystick, a mouse, a game pad, etc.), where these systems are capable of executing conventional software applications, such as "off-the-shelf" computer games or other software. In addition, each effector is modular in design, permitting a wide variety of system frames to be fashioned, based upon different combinations of the effectors, so as to facilitate isometric exercise of any desirable combination of muscle groups.

The above and still further objects, features and advantages of the present invention will become apparent upon consideration of the following detailed description of specific embodiments thereof, particularly when taken in conjunction with the accompanying drawings, wherein like reference numerals in the various figures are utilized to designate like components.

BRIEF DESCRIPTION OF THE DRAWINGS

FIG. 1 is a view in perspective of an interactive isometric exercise system in accordance with the present invention.

FIG. 2 is a view in perspective of another embodiment of an interactive isometric exercise system in accordance with the present invention.

DETAILED DESCRIPTION OF THE PREFERRED EMBODIMENTS

Figure 3:
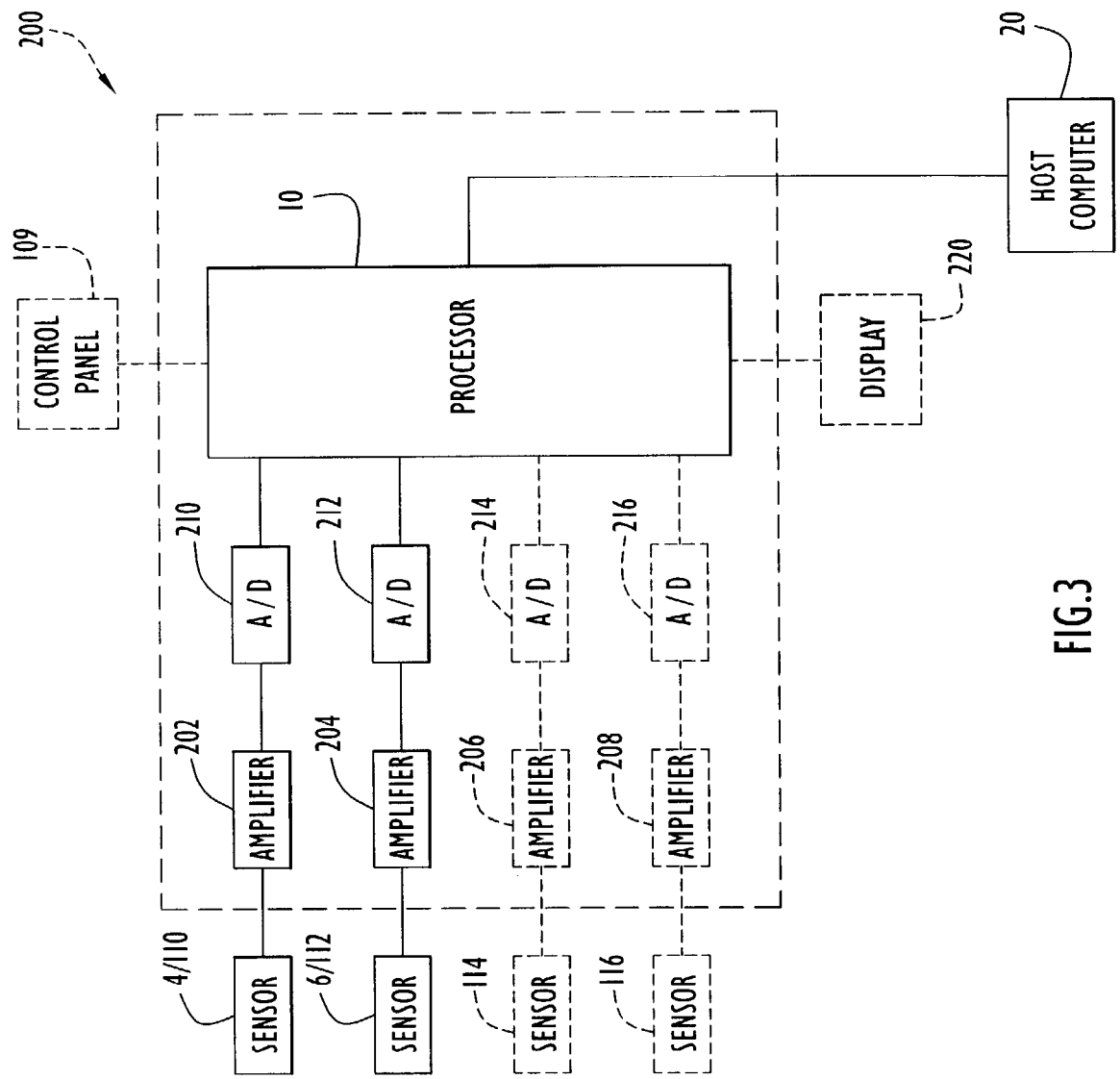
FIG. 3 is a schematic block diagram of an exemplary control circuit for the systems of FIGS. 1 and 2.

An interactive isometric exercise system according to the present invention is illustrated in FIG. 1. Specifically, system 1 includes an effector 2, preferably in the form of an elongated rod or bar, to measure a response to one or more amounts of force applied to the effector, and control circuitry 200 that communicates with the effector as well as a host computer system 20. The control circuitry includes a processor 10 (FIG. 3) that receives force measurement information from the effector and translates such information into data recognizable by the host computer system as described below. The processor may be implemented by any conventional or other microprocessor or circuitry. The host computer system is typically implemented by a conventional personal or other computer system (e.g., laptop, IBM compatible, Macintosh PC, PDA, etc.) including a base (e.g., including the processors, memories, software, etc.), keyboard, monitor and optional mouse or other input device. The host computer system executes a software application and facilitates user interaction with the application via the exercise system.

The effector includes an elongated and generally cylindrical bar or rod constructed of any suitably rigid material (e.g., a metal alloy) that is capable of being slightly deformed within its elastic limit in response to any combination of bending, twisting, tension and compression forces applied, for example, by the hands of a user to the bar. While depicted as a cylindrical bar, the effector may include any suitable geometric configurations (e.g., donut-shaped, U-shaped, V-shaped, etc.) with any selected type of exterior gripping surface (e.g., smooth, multifaceted, etc.). The amount and types of deformations applied to effector 2, which is proportional to the amount and types of straining forces applied by the user, is measurable by one or more sensors disposed at suitable locations on the effector bar as described below.

Exemplary sensors that are capable of measuring minute degrees of deflection of the effector along any number of different axes are strain gauge sensors. Strain gauges are well known for measuring strain applied to an object and are typically realized in the form of metallic wire or foil devices. When a strain gauge is applied in a suitable orientation to an exterior surface of an object, the strain gauge electrical resistance varies in proportion to the amount of a particular strain applied to the object. The change in resistance of the strain gauge is measurable (e.g., utilizing a conventional Wheatstone bridge configuration, where the strain gauge forms one of the resistors in the bridge). The Wheatstone bridge may be configured in any conventional manner to determine the change in resistance of the strain gauge. For example, when the object to which the strain gauge is applied undergoes a strain deformation, the change in resistance of the strain gauge can be easily determined by comparing a measured voltage across the bridge with a reference voltage and processing the voltage difference in a manner described below.

Two strain gauge sensors 4 and 6 are affixed on the effector outer surface near a central location of effector 2. The sensors are further aligned in a longitudinal direction of the effector bar and are offset from each other by approximately 90° on the outer periphery of the effector bar. By orienting effector 2 such that sensor 6 faces in a generally upward direction as depicted in FIG. 1, sensor 4 measures bending deflections of effector 2 in a generally horizontal plane about a horizontal axis X, while sensor 6 measures bending deflections of the bar in a generally vertical plane about a vertical axis Y. It is to be understood that the terms "upward", "downward", "top", "bottom", "side", "front", "rear", "upper", "lower", "vertical", "horizontal", "height", "width", "length" and the like are used herein merely to describe points of reference and do not limit the present invention to any specific orientation or configuration. Additional sensors may also be provided to measure compression, elongation, and twisting of the effector bar. For example, a third sensor may be affixed in a suitable alignment along the effector bar surface to measure twisting deflections of the effector bar with respect to the longitudinal dimension of the bar.

The sensors are connected to control circuitry 200 via individual wires, preferably disposed in a suitable sheath or conduit 8. The control circuitry is also connected, via a suitable connector 12, to a standard peripheral connection port (e.g., serial, parallel, USB, etc.) of host computer system 20. The control circuitry processor receives measured strain information from sensors 4 and 6 and converts such measured information into readable data packets for the host computer system as described below. The data packets are preferably configured to be indistinguishable from the inputs of any standard peripheral (e.g., a conventional mouse, joystick, game pad, etc.). In other words, effector 2 is physically manipulated by the user to effect the transfer of the same type of inputs from processor 10 to host computer system 20 that would normally be provided by a peripheral device to control operation of a software program running on the host computer system.

In operation, system 1 basically serves as a peripheral and sends the appropriate data to host computer system 20. In particular, the user orients effector 2 with sensor 6 facing generally upward, as described above, and holds the bar at its opposing ends with his or her hands. An appropriate amount of bending force is applied by the user to effector 2 using his or her hands to effect a minimal degree of horizontal bending of the effector in a particular direction and about the X axis as described above, with the resultant strain being applied to sensor 4. The measured strain is received by processor 10 of control circuitry 200 as a digital data value, as described below, and is placed into data packets. The data packets include a format resembling the data output from a conventional computer peripheral that is manipulated in a manner corresponding to that of the effector. Similarly, the application of force by the user to the effector to effect vertical bending of the effector bar in a particular direction about the Y axis results in data packets being sent by the processor to the host computer system. The data packets include a format resembling data output from a conventional computer peripheral that is manipulated in a manner corresponding to that of the effector. Combined applications of force by the user on the effector about both axes X and Y similarly result in data packets being sent by the processor to the host computer system in a format resembling corresponding movements of a conventional computer peripheral.

The data packets provided by processor 10 to host computer system 20 can be X and Y axis information typically provided by a computer peripheral for a computer game or other software providing images on a display screen 22 of the host computer system, where the axis information provided by the processor results in corresponding changes in the displayed images to reflect virtual movements within the virtual reality scenario. Thus, system 1 simulates the operability functions of a standard peripheral device, such as a joystick, while simultaneously achieving an isometric workout for various muscle groups of the user of the system. In addition, the system is operable with standard "off-the-shelf" gaming or other software programs that are designed for use with such standard peripheral devices.

The system described above may be modified to exercise multiple muscle groups of the user, separately or simultaneously, during operation of one or more software programs. Other components may also be provided to enhance system operation. For example, a display 220 (FIG. 3) may be coupled directly to the control circuitry processor to provide different forms of information, such as the amount and types of forces or the amount of total work applied by the user to the effector. Additional effectors may also be provided in the system to facilitate isometric exercise of differing muscle groups as well as simulating movements in multiple directions and other controlling features for a particular virtual reality scenario being executed by the host computer system. Further, exercise components, such as foot pedals in combination with a flywheel, may be provided to permit combinations of isokinetic, isotonic and isometric forms of exercise where the exercise components may further serve as other controls in a virtual reality scenario (e.g., a throttle to control the rate of traversal through the scenario, etc.).

Any number of effectors may be combined in any selected orientations, utilizing any suitable connectors (e.g., lug nuts, couplings, tee or wye fittings, cross fittings, etc.), to permit isometric exercise of one or more body parts depending upon a particular application. For example, a pair of effector bars, each including one or more strain sensors, may be connected to a base to form a T-bar configuration for a particular application, where the facing ends of the bars connect together with a T-type fitting and the fitting further connects with a bar extending from the base. The sensors on the bars can be coupled to a processor via a suitable wiring harness to facilitate processing of strain measurements into data packets that are recognizable by a host computer system as input data from a standard peripheral device. The effectors are essentially modular in design and may be connected via multiple extender rods or connectors in a variety of different configurations to achieve a variety of different applications as well as to permit customizing of the system to a particular individual's needs. By way of example, the effectors may each include a common length with one set of sensors that measure deformation in one axis (e.g., stretch/compression, bending, twisting, etc.). Two or more effectors may be connected to measure deformation in plural axes, while extender rods may be employed to construct a combined effector of a desired length. The effectors may be inserted into a base to which other elements (e.g., a seat, control circuitry, etc.) may be attached.

An exemplary embodiment of a "cockpit" type system configuration of effectors is illustrated in FIG. 2. Specifically, system 100 includes a frame with a base that engages a support surface and includes an elongated first base member 101 and an elongated second base member 102 attached at one end of the first base member to form a "T" configuration for the base, where the second base member is disposed at the front end of the base. Secured to an upper surface of the first base member near a rear end of the base is a seat 103 that faces toward the second base member and is configured to support a user in a seated position during system operation.

The frame further includes a set of elongated and generally cylindrical effector bars that form a T-type handle-bar configuration for manipulation by a user seated in seat 103. In particular, a first effector bar 104 extends at about a 45° angle from the front end of the base at the juncture of the first and second base members to a suitable location directly above a front portion of seat 103. Second and third effector bars 106 and 108 are secured at the free end of the first bar, via a suitable fitting 105 (e.g., tee, a lug, cross fitting, etc.), such that the second and third bars extend in opposing directions away from the first bar. A control panel 109 including one or more input devices (e.g., buttons, switches, a keypad, etc.) is secured at the fitting at the rear end of first bar 104 between the second and third bars so as to be accessible by the user during system operation. Each of the effector bars is preferably modular and constructed of a suitably rigid material (e.g., a metal alloy) that is capable of being slightly deflected within its elastic limit in response to any combination of bending, twisting, tension and compression forces applied by the user to the bars. While each of the effector bars is generally cylindrical, it is noted that the effector bars may be of any suitable shape (e.g., bent or curved, V-shaped, etc.) and have any suitable exterior surface geometries (e.g., curved, multifaceted, etc.).

At least one sensor is disposed on each effector bar for measuring at least one type of strain applied by the user to that bar. In particular, first bar 104 includes two strain gauge sensors 110 and 112 that are arranged at suitable locations on the outer surface of the first bar near the connection point of the first bar with the base and are angularly offset by approximately 90°. Sensors 110 and 112 measure the amount of a strain deformation applied to the first bar as a result of the user pushing or pulling on the second and/or third bars during system operation as described below. Similarly, the second and third bars each include a respective strain gauge sensor 114, 116 disposed at a suitable location on the outer bar surface near the connection point of each bar to the first bar. Sensors 114 and 116 measure the amounts of bending strain applied to the second and third bars along a horizontal axis when the user attempts to twist the second and/or third bars to simulate turning or steering of the handlebar configuration as described below.

The sensors are connected to processor 10 (FIG. 3) of control circuitry 200 via appropriate wiring harnesses. The control circuitry is secured to first base member 101 at a suitable location below first bar 104 and near the connection point of the first and second base members. However, it is noted that the control circuitry may be provided at any suitable location on the system frame or, alternatively, may be located separate from the system frame. The control circuitry is also connected, via a suitable connector 122, to a standard peripheral or other port (e.g., serial, parallel, USB, etc.) of host computer system 20. Strain gauge measurements that are received by processor 10 from the sensors are converted to information packets recognizable by the host computer system as described below. The host computer system displays a virtual reality scenario on display screen 22 that can be manipulated by the user in accordance with strain forces applied to the effector bars as described below. Optionally, display screen 220 (FIG. 3) may be coupled to the processor as described below and is provided at a suitable location on the system frame to be viewed by the user during system operation. The processor may control the display screen to display various information to the user (e.g., the degree of force applied to a particular effector bar at any given time, the amount of work performed by the user during a particular exercise session, and/or any other exercise or other related information). Further, the system may include other accessories (e.g., pedal or other exercise devices, etc.) to provide enhanced workouts. In addition, extender rods may be employed to configure the effector in accordance with user characteristics (e.g., height, reach, etc.).

An exemplary control circuit for the systems of FIGS. 1 and 2 is illustrated in FIG. 3. Specifically, control circuitry 200 includes a plurality amplifiers, a plurality of analog-to-digital (A/D) converters and processor 10. By way of example and with respect to the embodiment of FIG. 1, each sensor 4, 6 is connected to a respective amplifier 202, 204, which is in turn connected to a respective A/D converter 210, 212. Each A/D converter is further connected to processor 10. Similarly, and by way of example with respect to the embodiment of FIG. 2, each sensor 110, 112, 114, 116 is connected to a respective amplifier 202, 204, 206, 208, which is in turn connected to a respective A/D converter 210, 212, 214, 216. Each A/D converter is further connected to processor 10. Optionally, display 220, preferably mounted on the exercise system or in view of a user, is further connected to the processor to facilitate display of certain exercise or other related information as described above. As previously described, the processor is connected to a standard peripheral or other port of host computer system 20. A conventional power supply (not shown) provides appropriate power signals to each of the circuit components. The circuit may be powered by a battery and/or any other suitable power source. A power switch (not shown) may further be included to activate the circuit components.

One or more additional input devices may optionally be connected with the processor to enhance system operation. Examples of additional input devices include, without limitation, buttons, switches, a keypad, and aerobic resistance controllable devices, such as fly wheels coupled to foot pedals. Input devices such as buttons, switches, keypads, etc., provide information directly to the processor for placement in the data packets to be sent to the host computer system. By way of example, control panel 109 (FIG. 2), which includes input devices such as those previously described, is shown in circuit 200 as being connected to processor 10.

Each strain gauge sensor electrical resistance varies in response to compression and stretching of the associated effector bar. The amplifiers each basically arrange the corresponding sensor in a Wheatstone bridge configuration and determine the resistance change by comparing a measured voltage across the Wheatstone bridge with a reference voltage. The difference is amplified and typically in a range between zero and five volts. The amplified voltage value is sent by each amplifier to its respective A/D converter (e.g., a conventional A/D converter, such as National Semiconductor ADC08060) where the analog signal is converted to an eight-bit (e.g., signed or unsigned) or sixteen-bit (e.g., signed or unsigned) digital value. The digital value of each A/D converter is transmitted to a respective predetermined memory location in the processor. The processor samples the memory locations at predetermined time intervals, preferably on the order of ten milliseconds, to continuously process and send information to the host computer system to update and/or respond to an executing software application.

Basically, the amplified sensor value represents the force applied by the user, where values toward five volts indicate grater applied force. The amplified analog value is digitized or quantized within a range of 256 values (e.g., −127 to +127, eight bits signed) or 65,536 values (e.g., −32,767 to +32,767 sixteen bits signed) to indicate the magnitude and/or direction of the applied force. Thus, amplified voltage values toward five volts produce digital values toward the maximum values of the quantization ranges. The quantization may be performed by the A/D converters during the conversion, or by the processor.

Digital values received by the processor from the A/D converters, which correspond to strain measurements from the sensors, and values received from other optional input devices as noted above, are processed and arranged into suitable data packets for transmission to the host computer system. The processor may process the raw digital values in any fashion to account for various calibrations or to properly adjust the values within the quantization ranges as described above. The data packets are in a format resembling data input from a standard peripheral device (e.g., a mouse, a joystick, a game pad, etc.). For example, the processor may construct a USB data packet that includes the status of all input devices (e.g., buttons, etc.) and the values of each sensor. By way of example only, the data packet may include header information, X-axis information (e.g., eight bits signed) indicating a corresponding sensor force measurement along this axis, Y-axis information (e.g., eight bits, signed) indicating a corresponding sensor force measurement along this axis, rudder or steering information (e.g., eight bits, unsigned), throttle or rate information (e.g., eight bits, unsigned) and additional information relating to the status of input devices (e.g., buttons, etc.). Additional packet locations may be associated with data received from input devices connected with the processor, where the input devices represent additional operational criteria for the scenario (e.g., the firing of a weapon in the scenario when the user presses an input button, throttle, etc.). The host computer system processes the information or data packets in substantially the same manner as that for information received from a conventional peripheral to update and/or respond to an executing software application (e.g., game, etc.).

In operation, the user initially couples the system to a host computer system by connecting the control circuitry to the appropriate serial or other port of the host computer system utilizing the connector as described above. A software program is selected and run on the host computer system, and the user engages in a combined isometric exercise and interaction with the software program by gripping at least one effector bar and applying a force to exert a strain on the bar. The strain applied by the user causes at least one respective sensor to change in resistance. The change in resistance of the sensors is measured, amplified and converted into a digital value for transference to the processor. The processor processes and arranges the information into appropriate data packets to be sent to the host computer system as described above. The host computer system processes the information or data packets in substantially the same manner as that for information received from a conventional peripheral to update and/or respond to an executing software application (e.g., game, etc.).

An exemplary application for the system illustrated in FIG. 1 is a peripheral for a game or other virtual reality scenario being displayed on display screen 22 of host computer system 20. The user applies one or more bending forces to effector 2 with respect to at least one of the X and Y axes so as to effect corresponding movement, for example, of a character or an object in the scenario displayed by the host computer system. The digital data packets assembled by processor 10 for transference to host computer system 20 may be configured so that a bending force applied by the user to effector 2 with respect to the X axis results in a corresponding coordinate movement along a horizontal axis in the scenario displayed on display screen 22 (e.g., a movement to the left or to the right in the scenario). Similarly, a bending force applied to the bar with respect to the Y axis may result in a corresponding coordinate movement along a vertical axis in the displayed scenario (e.g., an up or down movement in the scenario). A combination of forces applied to the bar with respect to both X and Y axes would result in a corresponding movement along both the horizontal and vertical axes in the displayed scenario (e.g., a diagonal move).

In the system described above and illustrated in FIG. 2, the user operates system 100 in a seated position on seat 103, with the user's hands placed on second and third bars 106 and 108 at positions removed from fitting 105 and sensors 114 and 116. Application of a forward pushing or reverse pulling force (i.e., pushing bars 106, 108 away from or pulling those bars toward the user) results in a respective change in resistance of sensor 110 and/or sensor 112, which results in an appropriate digital data value being produced. The value is placed into data packets by processor 10 for transference to the host computer system as described above. Applying a bending force to second bar 106 and/or third bar 108 to effect bending of the bar along its longitudinal axis results in a respective change in resistance of sensor 114 and/or sensor 116, which results in appropriate digital data values being produced. The values are placed into data packets by processor 10 for transference to the host computer system as described above. The host computer system processes the information or data packets in substantially the same manner as that for information received from a conventional peripheral to update and/or respond to an executing software application (e.g., game, etc.).

As noted above, system 100 includes a "cockpit" frame design with a T-type handle bar configuration that is useful for a number of different virtual reality scenarios including, without limitation, flying and driving scenarios. In an exemplary flying scenario, the T-type handle bar may be implemented to function in the scenario as a conventional aircraft yolk. Diving (e.g., toward the ground) may be achieved in the flying scenario when the user indirectly applies a straining force to first bar 104 by attempting to push second and/or third bars 106 and 108 away from the user. Similarly, climbing (e.g., toward the sky) may be achieved in the flying scenario when the user applies a straining force to the second and/or third bars in an attempt to pull the bars toward the user. Rolling movements (e.g., rotations of the horizon representing a turning motion to the left or right) may be achieved in the flying scenario when the user applies corresponding bending forces to the second and/or third bars along their longitudinal axes in an attempt to rotate or turn the second and third bars in a clockwise or counterclockwise direction with respect to the first bar. Other features in the flying scenario, such as controlling flying speed, controlling flaps and/or spoilers, firing weapons, etc. may also be achieved utilizing input devices disposed on control panel 109 and/or additional input devices (e.g., additional effector bars for operation by the user's feet, foot pedals in combination with a flywheel, etc.). If the host computer system is linked to other systems (e.g., via a network of host computers or other communications medium), plural users may participate in the same virtual reality scenario session, thus facilitating competitive interaction (e.g., team races) between two or more users within the session.

In a driving scenario, system 100 may be configured to utilize the second and third bars as a steering wheel and throttle and brake combination. In particular, applying bending forces to the second and/or third bars to attempt a clockwise or counterclockwise rotation or turning of these bars with respect to the first bar would yield a corresponding right or left turn in the driving scenario. Accelerating and braking would be accomplished by a respective applied force to the second and/or third bars where the bars are either pushed away from or pulled toward the user. Additional features in the driving scenario, such as changing speed, controlling gears, the firing of weapons, etc. can be achieved utilizing additional input devices as described above.

As noted above, an optional display screen connected to the processor may be implemented to provide certain information, such as the level of exertion applied to a particular effector by the user as well as the amount of work done. Other features may also be displayed in relation to the exercise activities performed by the user during system operation.

The processor may further be configured to control the level of exertion required by a user for one or more effectors in order to achieve a particular response in the virtual reality scenario. For example, the processor may be configured to require a threshold resistance level be achieved, which is proportionate to the amount of straining force applied by the user to one or more effectors, before assigning appropriate data values to the data packets to be sent to the host computer. Threshold values for the change in strain gauge resistance may be input to the processor by the user via an appropriate input device (e.g., a keypad). Alternatively, or in combination with user input, the threshold values may be controlled by the processor based upon conditions within the virtual reality scenario, such as changing wind conditions, changing grade of the terrain (e.g., going uphill), etc. The processor may also control additional resistance type input devices, such as foot pedals, based upon the previously noted conditions in the virtual reality scenario.

The previously described systems provide an isometric exercise device that may be easily integrated to facilitate user interaction with "off-the-shelf" games or other software being executed on a host computer system in a manner that is indistinguishable from inputs generated by a standard peripheral device. The modular design of the effectors facilitates the assembly of a wide variety of different system designs utilizing any selected number and combination of effectors and sensors, where any one or more sensors may be provided for each effector to measure any number of selected types of strain forces applied to the effector by a user (e.g., bending forces, twisting forces, compression and tension forces). Thus, a user may customize the system to his or her needs and for a particular application. Systems may be designed that effect isometric exercise for any combination of body parts. In addition, input devices such as foot pedals may be incorporated into any system design to combine isometric exercise with isokinetic and/or isotonic exercises for a particular application.

It will be appreciated that the embodiments described above and illustrated in the drawings represent only a few of the many ways of implementing a computer interactive isometric exercise system and method for operatively interconnecting the exercise system to a computer system for use as a peripheral.

The exercise system and components (e.g., effectors, extenders, connectors, etc.) may be of any size or shape and may be constructed of any suitable materials. The effectors may be constructed of any suitable materials that preferably are subject to measurable deflection within an elastic limit of the materials when subjected to one or more straining or other forces by the user. The effectors may have any suitable geometric configurations, and two or more effectors may be combined in any suitable manner to yield a system frame that conforms to a desired design for a user for a particular application. Any suitable number of sensors may be applied to an effector to facilitate the measurement of any one or more types of strain or other forces applied by the user (e.g., bending forces, twisting forces, compression forces and/or tension forces).

Any suitable connector may be utilized to connect any two or more effectors together, including, without limitation, lug nuts, couplings, tee fittings, wye fittings and cross fittings. Any number of connectors may be utilized to form a system frame of effectors. The connectors may be constructed of any suitable materials. The frame may include any quantity of any type of seat or other user support structure disposed at any locations to support a user or user body portions.

Any suitable number of sensors may be utilized to measure any type of strain or other force applied to any suitable number of effectors. The sensors may be constructed of any suitable materials, may be disposed at any effector locations and may be of any suitable type (e.g., strain gauge, etc.). Further, the sensors may include any electrical, mechanical or chemical properties that vary in a measurable manner in response to applied force to measure force applied to an object.

The processor may be implemented by any quantity of any type of microprocessor or other circuitry, while the control circuitry may be disposed at any suitable locations on the system frame or, alternatively, remote from the system frame. The control circuitry and/or processor may communicate with the sensors via any suitable wiring or wireless connections. The control circuitry and/or processor may be connected to one or more host computer systems via any suitable peripheral or other port of the computer systems. The processor may further arrange digital data representing force measurements by sensors into any suitable data packet format that is recognizable by the host computer systems receiving data packets from the processor. The data packets may be of any desired length, include any desired information and be arranged in any desired format.

The processor may sample the measurements at any desired sampling rate (e.g., seconds, milliseconds, microseconds, etc.), or receive measurement values in response to interrupts. The analog values may be converted to a digital value having any desired quantity of bits or resolution. The processor may process the raw digital measurements in any desired fashion to produce information for transference to the host computer system. This information is typically dependent upon a particular application. For example, if a user applies medium force to an effector to indicate a right turn while depressing control panel buttons representing a wide open throttle and firing of weapons, the processor may process the data and assemble an exemplary data packet including a header (e.g., including a data packet identification or sequence indicator, a packet length, etc.), X and Y axes information each indicating a value in the range of fifty to eighty (e.g., which represents medium force for an eight bit signed value having a range of −127 to +127 and a rightward direction since the X and Y axes information include similar values), a throttle value of 255 (e.g. the maximum value for an eight bit unsigned value) and an appropriate bit set in a remaining packet byte indicating depression of the firing button. The correlation between the measured force and value for the X and Y axes or other information (e.g., throttle, steering, etc.) may be determined in any desired fashion. By way of example, the amplified measurement range may be divided into units corresponding to the resolution of the digital value. For an eight bit unsigned digital value (e.g., where the value indicates the magnitude of force), each increment represents $1/256$ of the voltage range. With respect to a five volt range, each increment is $5/256$ of a volt, which is approximately 0.02 volts. Thus, for an amplified force measurement of three volts, the digital value may correspond to approximately 150 (i.e., 3.0/0.2).

Any suitable number of any types of conventional or other circuitry may be utilized to implement the control circuit, amplifiers, sensors, A/D converters, and processor. The amplifiers may produce an amplified value in any desired voltage range, while the A/D converters may produce a digitized value having any desired resolution or quantity of bits (e.g., signed or unsigned). The control circuit may include any quantity of the above or other components arranged in any fashion. The resistance change of the sensors may be determined in any manner via any suitable conventional (e.g., Wheatstone bridge, etc.) or other circuitry. The amplifiers and processors may be separate within a circuit or integrated as a single unit. Any suitable number of any type of conventional or other displays may be connected to the processor to provide any type of information relating to a particular computer interactive isometric exercise session. A display may be located at any suitable location on or remote from the exercise system.

Any suitable number of additional input devices may be provided for the system to enhance virtual reality simulation scenarios. The input devices may be provided on any suitable number of control panels that are accessible by the user during system operation and have any suitable configuration (e.g., buttons, switches, keypads, etc.). Optionally, input devices may be provided (e.g., foot pedals, stairs, ski type exercisers, treadmills, etc.) that provide isokinetic and/or isotonic exercise features in addition to the isometric exercise features provided by effectors. The additional exercise input devices may further be resistance controlled by the processor.

The host computer system may be implemented by any quantity of any personal or other type of computer or processing system (e.g., IBM-compatible, Apple, Macintosh, laptop, palm pilot, microprocessor, etc.). The host computer system may include any commercially available operating system (e.g., Windows, OS/2, Unix, Linux, etc.), any commercially available and/or custom software (e.g., communications software, application software, etc.) and any types of input devices (e.g., keyboard, mouse, microphone, voice recognition, etc.). It is to be understood that the software of the exercise system and/or processor may be implemented in any desired computer language, and could be developed by one of ordinary skill in the computer and/or programming arts based on the functional description contained herein. Further, any references herein of software performing various functions generally refer to computer systems or processors performing those functions under software control. The processor may alternatively be implemented by hardware or other processing circuitry, or may be implemented on the host computer system as software and/or hardware modules receiving the sensor measurements. The various functions of the processor may be distributed in any manner among any quantity (e.g., one or more) of hardware and/or software modules or units, computer or processing systems or circuitry, where the computer or processing systems or circuitry may be disposed locally or remotely of each other and communicate via any suitable communications medium (e.g., LAN, WAN, Intranet, Internet, hardwire, modem connection, wireless, etc.). The software and/or algorithms described above may be modified in any manner that accomplishes the functions described herein.

From the foregoing description, it will be appreciated that the invention makes available a novel computer interactive isometric exercise system and method for operatively interconnecting the exercise system to a computer system for use as a peripheral, wherein an isometric exercise system serves as a peripheral to facilitate user interaction with a host computer system.

Having described preferred embodiments of a novel computer interactive isometric exercise system and method for operatively interconnecting the exercise system to a computer system for use as a peripheral, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. An isometric exercise system serving as a peripheral to manipulate a virtual reality scenario of a host processing system in accordance with user exercise, comprising:
   a frame to support a user;
   an effector to provide an isometric exercise for said user, wherein said effector is fixedly secured to said frame and includes an elongated rod;
   at least one sensor coupled to said rod and responsive to at least one force applied by said user to said effector to perform said isometric exercise, wherein said applied force effects a measurable deformation of said rod that is measured by said at least one sensor; and
   a processor coupled to said at least one sensor and including a data processing module to receive and process data corresponding to applied force information measured by said at least one sensor and to transfer information to said host processing system to control said virtual reality scenario of said host processing system in accordance with performance of said isometric exercise and manipulation of said effector by said user.

2. The system of claim 1, wherein said frame includes a plurality of effectors securable to each other via at least one connector.

3. The system of claim 2, wherein orientation of said effectors in said frame is selectively adjustable to permit customization of said frame based upon a user preference.

4. The system of claim 1, wherein said frame includes a body support to support at least one user and a base with said effector extending from said base of said frame.

5. The system of claim 1, further comprising:
   a display controlled by said processor to output information relating to effector manipulation by said user during system operation.

6. The system of claim 1, further comprising:
   at least one input device to provide additional information to said processor for processing and transference to said host processing system.

7. The system of claim 1, wherein said system includes at least one input device that is manipulable by said user to effect at least one of isokinetic and isotonic exercise by said user during system operation.

8. The system of claim 1, wherein said effector facilitates isometric exercise of muscle groups associated with a plurality of body parts in response to effector manipulation by said user.

9. A method of performing an isometric exercise utilizing a system that serves as a peripheral to manipulate a virtual reality scenario of a host processing system, wherein said system includes a frame to support a user, an effector including an elongated rod, at least one sensor coupled to said rod, and a processor, the method comprising:
   (a) measuring at least one force applied by a user to said effector, wherein said effector provides an isometric exercise for said user and is fixedly secured to said frame, and wherein said applied force effects a measurable deformation of said rod that is measured by said at least one sensor;
   (b) processing data corresponding to applied force information measured by said at least one sensor; and
   (c) transferring information from said processor to said host processing system to control said virtual reality scenario of said host processing system in accordance with performance of said isometric exercise and manipulation of said effector by said user.

10. The method of claim 9, wherein step (a) further includes:
   (a.1) securing a plurality of effectors to each other via at least one connector within said frame.

11. The method of claim 10, wherein step (a.1) further includes:
   (a.1.1) selectively orienting said effectors in said frame to permit customization of said frame based upon a user preference.

12. The method of claim 9, wherein step (a) further includes:
   (a.1) providing a body support to support said user on said frame; and
   (a.2) providing a base for said frame with said effector extending from said base of said frame.

13. The method of claim 9, wherein said system further includes a display controlled by said processor, and the method further comprises:
   (d) displaying output information, via said display, relating to manipulation of said effector by said user during system operation.

14. The method of claim 9, wherein said system further includes at least one input device, and the method further comprises:
   (d) providing additional information, input by said at least one input device to said processor, for processing and transference to said host processing system.

15. The method of claim 9, wherein said system includes at least one input device, and the method further comprises:
   (d) facilitating at least one of isokinetic and isotonic exercise by said user during system operation via manipulation of said at least one input device.

16. The method of claim 9, further comprising:
   (d) facilitating isometric exercise of muscle groups associated with a plurality of body parts in response to manipulation of said effector by said user.

17. The system of claim 1, wherein, during system operation, said processor further selectively adjusts an amount of said at least one force that must be applied by said user to said effector to facilitate user interaction with said host processing system in response to manipulation of said effector by said user.

18. The system of claim 17, further comprising:
an input device to input to said processor the amount of said at least one force that must be applied by said user.

19. The system of claim 5, wherein said processor further determines an amount of work applied by said user to said effector for a selected period of time during system operation and controls said display to output information relating to the amount of work applied by said user.

20. The method of claim 9, further comprising:
(d) selectively adjusting an amount of said at least one force that must be applied by said user to said effector to facilitate user interaction with said host processing system in response to manipulation of said effector by said user.

21. The method of claim 20, wherein step (d) includes:
(d.1) facilitating user input of the amount of said at least one force that must be applied by said user.

22. The method of claim 13, wherein step (b) further includes:

(b.1) determining, via said processor, an amount of work applied by said user to said effector for a selected period of time during system operation; and
wherein step (d) includes:
(d.1) displaying output information, via said display, relating to the amount of work applied by said user to said effector.

23. The system of claim 1, wherein said data processing module produces said information in a format resembling data output from a host processing system peripheral.

24. The system of claim 1, wherein said effector provides an isometric exercise for a user upper body portion.

25. The method of claim 9, wherein step (c) further includes:
(c.1) transferring said information in a format resembling data output from a host processing system peripheral.

26. The method of claim 9, wherein said effector provides an isometric exercise for a user upper body portion.

27. The system of claim 1, wherein said virtual reality scenario includes a gaming scenario.

28. The method of claim 9, wherein said virtual reality scenario includes a gaming scenario.

* * * * *

US007121982C1

(12) INTER PARTES REEXAMINATION CERTIFICATE (833rd)
United States Patent
Feldman

(10) Number: US 7,121,982 C1
(45) Certificate Issued: Mar. 3, 2014

(54) COMPUTER INTERACTIVE ISOMETRIC EXERCISE SYSTEM AND METHOD FOR OPERATIVELY INTERCONNECTING THE EXERCISE SYSTEM TO A COMPUTER SYSTEM FOR USE AS A PERIPHERAL

(75) Inventor: Philip Feldman, Catonsville, MD (US)

(73) Assignees: Nintendo, Co., Ltd., Kamitoba Minami-Ku, Kyoto (JP); Nintendo of America, Inc.

Reexamination Request:
No. 95/001,460, Oct. 1, 2010

Reexamination Certificate for:
Patent No.: 7,121,982
Issued: Oct. 17, 2006
Appl. No.: 10/309,565
Filed: Dec. 4, 2002

(51) Int. Cl.
*A63B 21/00* (2006.01)

(52) U.S. Cl.
USPC .................. 482/8; 482/1; 482/9; 482/900

(58) Field of Classification Search
None
See application file for complete search history.

(56) References Cited

To view the complete listing of prior art documents cited during the proceeding for Reexamination Control Number 95/001,460, please refer to the USPTO's public Patent Application Information Retrieval (PAIR) system under the Display References tab.

*Primary Examiner* — William Doerrler

(57) ABSTRACT

A computer interactive isometric exercise system includes an effector, a sensor coupled at a selected location on the effector to measure a force applied by a user to the effector, where the applied force effects a strain on the effector, and control circuitry. The control circuitry includes a processor that receives and processes data corresponding to applied force information measured by the sensor for transference to a host computer. The processed data is transferred in a format compatible with the host computer and facilitates user interaction with the host computer in response to effector manipulation by the user. A plurality of effectors may further be combined together to form a system frame that provides a variety of isometric exercises for the user in combination with user interaction with the host computer.

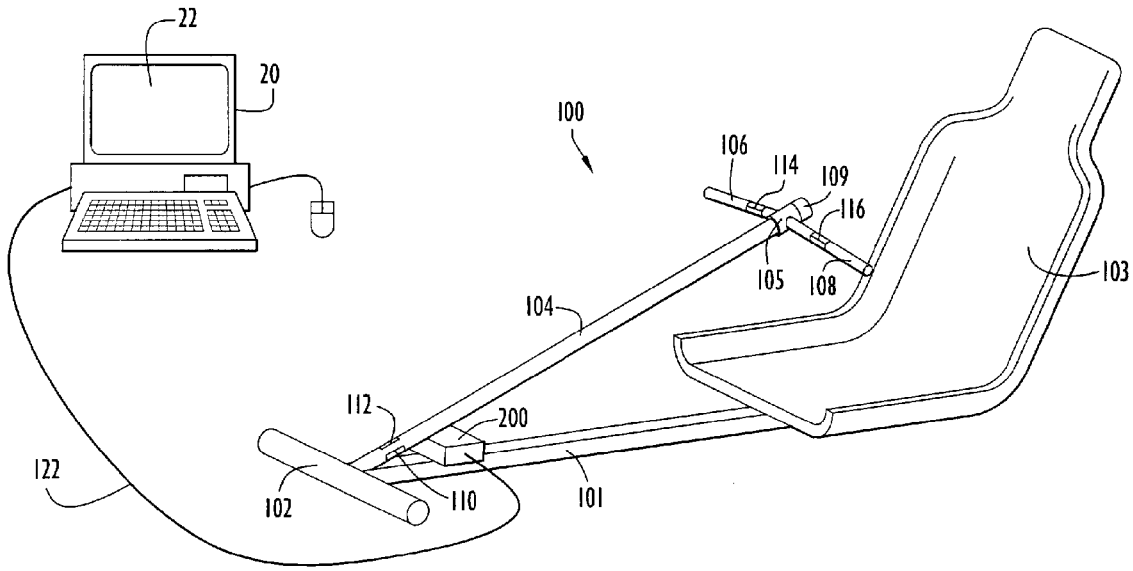

INTER PARTES REEXAMINATION CERTIFICATE ISSUED UNDER 35 U.S.C. 316

NO AMENDMENTS HAVE BEEN MADE TO THE PATENT

AS A RESULT OF REEXAMINATION, IT HAS BEEN DETERMINED THAT:

The patentability of claims 1-28 is confirmed.

* * * * *